United States Patent
Boyles et al.

(10) Patent No.: US 6,450,994 B1
(45) Date of Patent: Sep. 17, 2002

(54) STORAGE AND DELIVERY OF MULTI-DOSE, PRESERVATIVE-FREE PHARMACEUTICALS

(75) Inventors: James V. C. Boyles, San Diego, CA (US); John S. Kent, Newport Coast, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 09/526,052

(22) Filed: Mar. 15, 2000

(51) Int. Cl.[7] .............................................. A61M 35/00

(52) U.S. Cl. ..................... 604/294; 604/295; 604/298; 604/300; 222/420; 222/494; 428/35.2; 428/35.4; 428/214

(58) Field of Search .................. 604/294–300; 222/340, 387, 420, 421, 494; 428/35.2, 35.4, 214, 215, 423.5, 424.8, 475.8, 476.3; 383/113, 116

(56) References Cited

U.S. PATENT DOCUMENTS

| | | | |
|---|---|---|---|
| 4,686,125 A | 8/1987 | Johnston et al. | 428/35 |
| 4,692,361 A | 9/1987 | Johnston et al. | 428/35 |
| 5,320,845 A | 6/1994 | Py | 424/427 |
| 5,588,560 A | 12/1996 | Benedict et al. | 222/106 |
| 5,613,957 A | 3/1997 | Py | 604/294 |
| 5,685,869 A | 11/1997 | Py | 604/294 |

*Primary Examiner*—Charles R. Eloshway
*Assistant Examiner*—Tuan Nguyen
(74) *Attorney, Agent, or Firm*—Walter A. Hackler

(57) ABSTRACT

Apparatus for multi-dose delivery of preservative-free pharmaceuticals includes a film laminate flexible container for holding and maintaining a sterile drug formulation. A nozzle disposed within the container and in fluid communication therewith provides for dropwise dispensing of the formulation from the flexible container. The nozzle includes an interface established by inner and outer portions of the nozzle which is normally sealed. The nozzle out of portion is sufficiently flexible to enable expansion thereof and passage of the dry formulation therethrough by a piston which withdraws selected volumes of the formulation from the container.

16 Claims, 1 Drawing Sheet

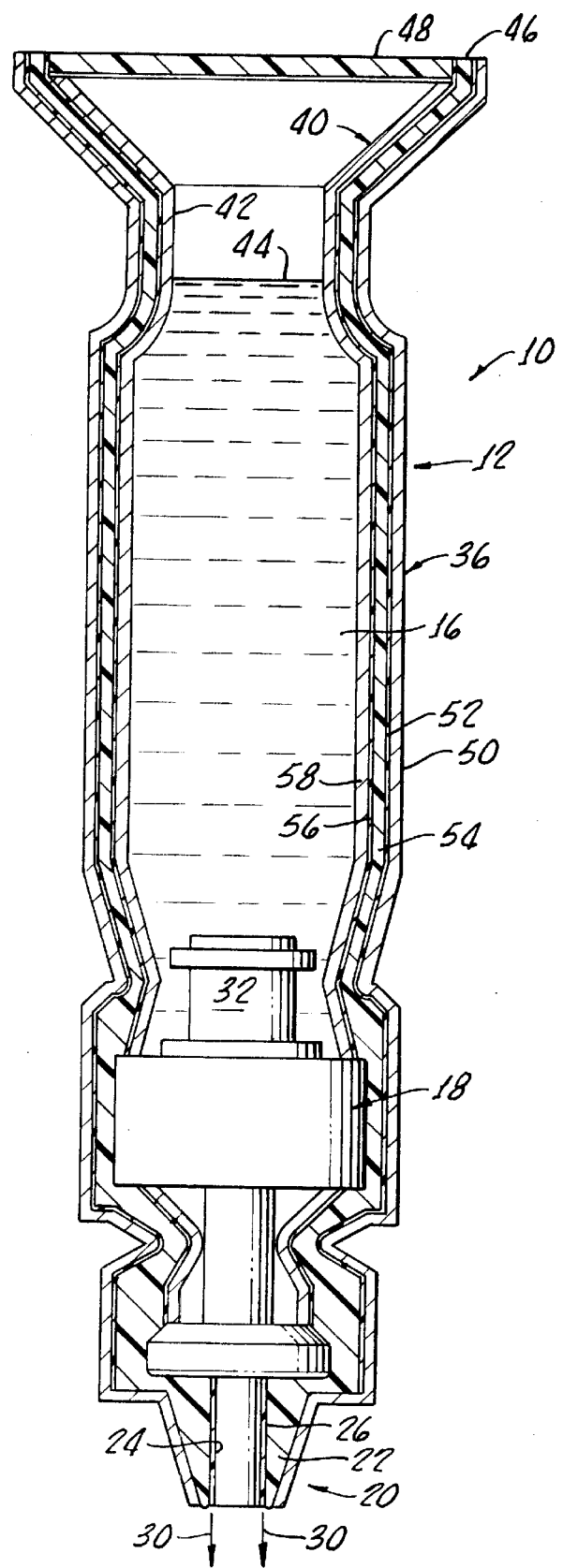

STORAGE AND DELIVERY OF MULTI-DOSE, PRESERVATIVE-FREE PHARMACEUTICALS

The present invention is generally directed to a flexible container or bottle and more particularly relates to apparatus for instilling a medicament into an eye.

A great number of devices have been developed for instilling medicament to an eye. Well known eye drop containers conventionally include a squeezable container and a nozzle for releasing drops of medicament into the eye by compression of the container.

It is well known that such containers must be formed from materials having little or no interaction with the intended contents of the container or bottle both in order to prevent contamination of the contained fluid and the leakage of fluids through the bottle. This selection of container materials is particularly important for drug/pharmaceutical products since changes in a particular drug formulation due to impurities introduced by or through the container wall, and changes in the drug formulation over time due to migration of various components through the container walls can have a profound effect on the products' performance in both physical and chemical terms.

These effects are commonly observed with flexible containers such as I/V infusion bags and multidose nonpreserved and preserved drug delivery systems. An improper selection of container materials can result in water/weight loss, gas permeability, drug instability and drug absorption and adsorption. The problem, of course, is more acute for flexible or pliable containers designed for the dispensing of formulations contained therein. Most polymers suitable for the construction of flexible containers, such as polyethylene, Kraton, C-Flex, Sarlink, are not suitable due to the absorption or permeation of drug formulations therethrough.

When preservative-free medicaments are utilized, simple eye drop dispensers are not practical because there are no means for preventing the tip from being contaminated due to its exposure to air. Such tip contamination ultimately spreads to the medicament in the container.

In an attempt to overcome these problems, apparatus has been developed for applying a medicament to an eye which includes a nozzle having a seam which is normally in a closed position for preventing the passage of medicament through the nozzle, and which opens in response to a flow of medicament of sufficient pressure to enable opening of the seam in order to permit the passage of medicament through the nozzle for release into the eye, see U.S. Pat. No. 5,685,869.

While this nozzle is suitable, it is necessary to provide a suitable reservoir of medicament in order to create a working, producible device for multiple dose delivery of a preservative-free product of sufficient dose accuracy for consumer benefit and regulatory body registration over an extended period of time of up to six months or more.

Operation of prior art devices such as set forth in the hereinabove referenced U.S. patent, typically causes a small negative pressure, or vacuum, within the medicament container during operation. When a collapsible container is utilized to accommodate shrinking of volume of the medicament reservoir, the materials of construction may not satisfactorily inhibit the permeation of air through the container walls to provide a desired long term use in storage of the device without contamination of the stored medicament.

The present invention overcomes the shortcomings of the prior art devices by providing nozzle and medicament reservoir combination which enables multiple dose delivery of a preservative-free product with accurate dose dispensing over extended periods of time.

SUMMARY OF THE INVENTION

Apparatus is provided in accordance with the present invention for, multi-dose delivery of preservative-free pharmaceuticals. Generally, apparatus includes a flexible container which provides a means for holding and maintaining a sterile drug formulation. To achieve this result, the flexible container is formed from a film laminate as hereinafter described in greater detail.

Nozzle means are provided and disposed in fluid communication with the flexible container for dropwise dispensing of the formulation from the flexible container. The nozzle means includes an outer nozzle portion and an inner nozzle portion received within the outer nozzle portion. This combination provides a normally sealed interface therebetween and, importantly, the nozzle portion is sufficiently flexible to enable expansion thereof and passage of drug formulation thereto. The passage of drug formulation occurs when sufficient pressure is provided. This pressure is provided by a piston which forces metered amounts of formulation from the flexible container through the interface.

More particularly, the flexible container includes a film laminate having sufficient flexibility to collapse in volume upon withdrawal of formulation therefrom by'the piston. This prevents any pressure differential occurring across the film laminate which further ensures not only operation of the piston but prevention of any air permeation of the film laminate due to such pressure.

The piston means is sized for releasing a selected volume formulation into an eye. For ease of manufacture, the flexible container in the outer nozzle portion are intricately formed and the piston means is disposed within the flexible container.

Still more particularly, in accordance with the present invention, the film laminate may include a layer of linear load density polyethylene for forming an outside layer of the flexible container, a layer of biaxially oriented nylon for forming a core layer of the flexible container and a layer of linear low density polyethylene for forming an inside layer of the flexible container. The outside and the inside layer are bonded to the core layer by separate layers of polyurethane adhesive.

Further, the film structure may include and outside and inside polyethylene layer with a density of between about 0.91 to about 0.94 g/cm$^3$. Further, the outside layer may include approximately 0.05% to about 0.15% by way of a fatty acid amide containing 8 to 22 carbon atoms. Still more specifically, the fatty acid amide may be an oleic amide.

The outside layer may have a coefficient friction of between about 0.2 to 0.4 and the polyurethane adhesive may comprise a polyestra-urethanediol resin.

In addition, to maintain integrity of the film laminate, the inside and outside layers may be bonded to the core layer where at least 500 gms/inch of force as a delimination strength. Further, to prevent oxidation, the inside low density polyethylene may include an antioxidant, a stabilizer and an anti-blocking agent.

BRIEF DESCRIPTION OF THE DRAWINGS

The advantages and features of the present invention will be better understood by the following description when considered in conjunction with the accompanying drawing:

FIG. 1 is a cross sectional view of the apparatus in accordance with the present invention for multi-dose delivery of preservative-free pharmaceuticals.

DETAILED DESCRIPTION

With reference to FIG. 1, there is shown apparatus 10 in accordance with the present invention for multi-dose delivery of preservative-free pharmaceuticals. The apparatus generally includes a flexible container 12 which provides a means for holding and maintaining a sterile drug formulation 16. The flexible container is formed from a film laminate as hereinafter described in greater detail. A nozzle 20, disposed in fluid communication with the flexible container 12, is provided for dropwise dispensing of formulation 16 from the flexible container 12.

The nozzle 20 includes an outer nozzle portion 22 and an inner nozzle portion 24. As shown, the inner nozzle portion 24 is received within the outer nozzle portion 22 to provide a normally sealed interface 26 therebetween. The nozzle outer portion 22 and flexible container 12 are integrally formed with a thickness of the outer nozzle portion 22 being sufficiently flexible to enable expansion thereof and passage of drug formulation 16 therepast as indicated by the arrows 30.

The nozzle means incorporates a pump 32 for forcing metered amounts of formulation from the flexible container 12 through the interface 26 and preferably is sized for releasing a selected volume of formulation into an eye. As shown, the pump 32 is disposed within the flexible container 12 and may be constructed in accordance with U.S. Pat. No. 5,613,957 entitled, APPARATUS FOR APPLYING MEDICAMENT TO AN EYE, this patent being incorporated herewith in its entirety including drawings and specification, for the purpose of describing a pump, or piston means for forcing formulation from the container 12 through the interface 26 in accordance with the present invention.

Generally, the container 12 is sized and shaped for facilitating easy handling and the container wall 36 if formed with a thickness suitable for use in the present invention.

The container 12 may include a funnel 40 suitable for filling the pouch 12 through a neck 42 to a suitable liquid level 44 from the pouch end 46. An end, or seal, 48 is provided at the container end 46 for sealing the formulation 16 within the container 12.

Preferably, the container, including the wall 36 and nozzle outer portion 22, are formed from a film laminate disclosed in U.S. Pat. Nos. 4,686,125 and 4,692,361, both of which are incorporated herewith in their entirety for the purpose of describing a suitable container 12 material.

In that regard the container wall 36 includes an outside layer 50, a first adhesive layer 52, a core layer 54, a second adhesive layer 56 and an inside layer 58. The adhesive layers 52, 56 bond the outside and inside layers 50, 58 to the core layer 54.

The outside and inside layers 50, 58 are constructed from polyethylene. Preferably, the outside and inside layers 50, 58 are a linear low density polyethylene. As used herein, linear low density means that the polyethylene is made by low pressure polymerization and has a density of between approximately 0.91 to about 0.94 grams/cubic centimeter. The preferred density of the linear density polyethylene is between approximately 0.915 to about 0.930.

The preferred linear low density polyethylene contains approximately 2% to about 10% by weight 1-hexene. In a most preferred embodiment, the polyethylene contains approximately 5% by weight 1hexene. Other olefinic comonomers with 4 to 18 carbon atoms also function satisfactorily. Examples of these olefins are 1-octene, 1-butene, 1-pentene, and 4-methyl-1-pentene which may be present as approximately 5% to about 11% by weight of the linear low density polyethylene.

Preferably, the container 12 is made with a commercial packaging machine and accordingly, it is important that the outside layer 50 has a sufficiently low coefficient of friction. The outside layer 50 must have a low coefficient of friction to ensure that it flows smoothly through the processing machine, e.g., a form, fill and seal packaging machine. Preferably, the outside layer has a coefficient of friction of approximately 0.2 to about 0.4 as measured by ASTM test D-1894 between the outside layer and a stainless steel surface. The preferred coefficient of friction of the outside layer 4 is approximately 0.25.

To provide the linear low density polyethylene with a sufficiently low coefficient of friction, the polyethylene is slip modified by adding a fatty acid amide additive that acts like a lubricant and lowers the coefficient of friction of the film. The preferred fatty acid amides have 8 to 22 carbon atoms. Oleic amide has been found to modify the linear low density polyethylene sufficiently to produce the required. coefficient of friction. Preferably approximately 0.03% to about 0.15% by weight of oleic amide is added to the linear low density polyethylene.

The thickness of the wall 36 with layers 50, 54, 58 is selected to provide flexibility to the container 12. Preferably, the outside layer 50 and inside layer 58 have a thickness of between approximately 40 to about 100 microns. The preferred thickness of the outside and inside layers 50, 58 is between approximately 50 and about 70 microns. This thickness affords: a good seal, good clarity, pinhole resistance, a good tensile strength, sufficient impact strength and provides good flexibility for the container 12.

Preferably, the outside layer and inside layer 50, 58 contain an antioxidant.

The linear low density polyethylene preferably also contains a stabilizer and an antiblocking agent. The stabilizer provides needed properties during the production of the film from the resin pellets. Preferably the stabilizer is calcium stearate and comprises approximately 0.02% to about 0.06% by weight of the polyethylene copolymer. The antiblocking agent prevents the film from sticking together. Preferably the antiblocking agent is magnesium silicate and comprises approximately 0.11% to about 0.15% by weight. Other antiblocking agents that have been found to produce satisfactory results are aluminum hydroxide and magnesium hydroxide.

The core layer 54 of the present invention is a polyamide, preferably nylon. The preferred nylon for the core layer 54 is a biaxially oriented nylon. A biaxially oriented nylon 6, such as the one manufactured by Unitika Ltd. of Osaka, Japan, has been found to produce satisfactory results. Other nylons may also be utilized, preferably low extractable nylons, examples of such nylon and cast nylon, nylon 6-6, nylon 11, and nylon 12. All of these nylons may be either oriented or cast nylons.

As used herein, biaxially oriented nylon means that the nylon film has been extruded and stretched in both directions. This ensures that the molecules of nylon are biaxially oriented. This provides the container 12 with increased mechanical qualities, i.e., pinhole resistance, tear resistance, (resistance to the art of a tear), and stretch resistance.

Preferably, the core layer 54 has a thickness of between approximately 10 to about 40 microns. The preferred thickness of the core layer is approximately 15 to about 20 microns in the wall 36 area. The thickness of the core layer 54 as part of the nozzle outer portion 22 may be up to 0.15 inches so as to provide an expandable interface with the nozzle inner portion 24, the nozzle inner portion being more rigid than the combined layers 50, 54, 58.

The first adhesive layer 52 bonds the outside layer 50 to the core layer 54 and the second adhesive layer 56 bonds the inside layer 58 and core layer 54 to each other. Preferably, the adhesive is an aliphatic polyurethane. The preferred aliphatic polyurethane is a polyester-urethanediol resin manufactured by Takeda Chemical Industries Co., Ltd. under the name Takelac A-38 or Takelac A-520.

The adhesive layers 52 and 56 create a strong bond between the polyethylene layers 50 and 58 and the core layer 54. Preferably, the bond strength is at least 500 gms/inch of force. Most preferably, the bond strength is at least 700 gms/inch of force. The aliphatic polyurethane adhesive layers 50 and 58 also provide the following desirable properties to the laminate film structure 10: transparency, flexibility, low temperature resistance, processability, and initial tackiness.

The preferred thickness of each of the adhesive layers 52 and 56 is approximately 1 to about 10 microns. The most preferred thickness of each of the adhesive layers 52 and 56 is approximately 3 to about 5 microns.

The film laminate 10 of this invention is preferably produced by dry lamination. Preferably, the dry lamination process utilizes a two-component curing system. The adhesive is tacky at the time of combination, and is cured at room temperature.

Although there has been hereinabove described apparatus for multi-dose delivery of preservative-free pharmaceuticals in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. Apparatus for multi-dose delivery of preservative-free pharmaceuticals, said apparatus comprising:
    flexible container means for holding and maintaining a sterile drug formulation; and
    nozzle means, disposed in fluid communication with said flexible container means, for dropwise dispensing of the formulation from said flexible container means, said nozzle means including an outer nozzle portion and an inner nozzle portion received within the outer nozzle portion to provide a normally sealed interface therebetween, said nozzle outer portion being sufficiently flexible to enable expansion thereof and passage of drug formulation therethrough, said flexible container means and said outer nozzle portion being integrally formed from a continuous film laminate.

2. The apparatus according to claim 1 wherein said nozzle means comprises piston means for forcing formulation from said flexible container means through said interface.

3. The apparatus according to claim 2 wherein said flexible container means includes film laminate having sufficient flexibility to collapse in volume upon withdrawal of formulation therefrom by said piston means.

4. The apparatus according to claim 3 wherein said piston means is sized for releasing a selected volume of formulation into an eye.

5. The apparatus according to claim 4 wherein said piston means is disposed within said flexible container means.

6. The apparatus according to claim 5 wherein said film laminate comprises:
    a layer of a linear low density polyethylene for forming an outside layer of the flexible container;
    a layer of biaxially oriented nylon for forming a core layer of the flexible container;
    a layer of a linear low density polyethylene for forming an inside layer of the flexible container; and
    the outside layer and inside layer being bonded to the core layer by separate layers of polyurethane adhesive.

7. The film structure of claim 6 wherein the outside and inside polyethylene layers have a density of between approximately 0.91 to about 0.94 g/cm$^3$.

8. The film structure of claim 6 wherein the outside layer includes approximately 0.05% to about 0.15% by weight of a fatty acid amide containing 8 to 22 carbon atoms.

9. The film structure of claim 8 wherein the fatty acid amide is an oleic amide.

10. The film structure of claim 6 wherein the outside layer has a coefficient of friction of between 0.2 to 0.4.

11. The film structure of claim 6 wherein the polyurethane adhesive comprises a polyester-urethanediol resin.

12. The film structure of claim 11 wherein the inside an outside layers are bonded to the core layer with at least 500 gms/inch of force as delamination strength.

13. The film structure of claim 6 wherein the outside and inside linear low density polyethylene includes: an antioxidant; a stabilizer; and an antiblocking agent.

14. Apparatus for multi-dose delivery of preservative-free pharmaceuticals, said apparatus comprising:
    flexible container means for holding and maintaining a sterile drug formulation, said flexible container means being formed from a film laminate, said film laminate comprising:
    a layer of a linear low density polyethylene for forming an outside layer of the flexible container, a layer of biaxially oriented nylon for forming a core layer of the flexible container, a layer of a linear low density polyethylene for forming an inside layer of the flexible container, and the outside layer and inside layer being bonded to the core layer by separate layers of polyurethane adhesive; and
    nozzle means, disposed in fluid communication with said flexible container means, for dropwise dispensing of the formulation from said flexible container means, said nozzle means including an outer nozzle portion and an inner nozzle portion received within the outer nozzle portion to provide a normally sealed interface therebetween, said nozzle outer portion being sufficiently flexible to enable expansion thereof and passage of drug formulation therethrough, said nozzle means comprising piston means, disposed in said flexible container means, for forcing formulation from said flexible container means through said interface, said flexible container means and said outer nozzle being integrally and continuously formed from said film laminate.

15. The apparatus according to claim 14 wherein said flexible container means includes film laminate having sufficient flexibility to collapse in volume upon withdrawal of formulation therefrom by said piston means.

16. The apparatus according to claim 15 wherein said piston means is sized for releasing a selected volume of formulation into an eye.

* * * * *